(12) United States Patent  
Heywood et al.

(10) Patent No.: US 8,930,224 B2  
(45) Date of Patent: *Jan. 6, 2015

(54) PERSONALIZED MANAGEMENT AND COMPARISON OF MEDICAL CONDITION AND OUTCOME BASED ON PROFILES OF COMMUNITY PATIENTS

(75) Inventors: Benjamin Heywood, Newton, MA (US); Jeff Cole, Newton, MA (US); James Heywood, Newton, MA (US)

(73) Assignee: PatientsLikeMe, Inc., Cambridge, MA (US)

( * ) Notice: Subject to any disclaimer, the term of this patent is extended or adjusted under 35 U.S.C. 154(b) by 56 days.

This patent is subject to a terminal disclaimer.

(21) Appl. No.: 13/446,797

(22) Filed: Apr. 13, 2012

(65) Prior Publication Data

US 2013/0066652 A1     Mar. 14, 2013

Related U.S. Application Data

(63) Continuation of application No. 12/251,031, filed on Oct. 14, 2008, now Pat. No. 8,160,901, which is a continuation of application No. PCT/US2008/079673, filed on Oct. 12, 2008.

(60) Provisional application No. 60/998,768, filed on Oct. 12, 2007, provisional application No. 60/998,669, filed on Oct. 12, 2007, provisional application No. 61/070,067, filed on Mar. 20, 2008.

(51) Int. Cl.  
*G06F 19/00*     (2011.01)

(52) U.S. Cl.  
USPC ................................................. 705/3

(58) Field of Classification Search  
USPC ................................................. 705/3  
See application file for complete search history.

(56) References Cited

U.S. PATENT DOCUMENTS 5,594,638 A * 1/1997 Iliff ................................. 705/3  
6,081,786 A * 6/2000 Barry et al. .................... 705/3

* cited by examiner

*Primary Examiner* — John Pauls  
(74) *Attorney, Agent, or Firm* — Edwards Wildman Palmer LLP; Ralph A. Loren; Jonathon P. Western

(57) ABSTRACT

The invention can be directed toward a method for personalized management and comparison of medical condition and outcome based on patient profiles of a community of patients. The method can include the steps of providing a database of patient profiles, providing a user interface for inputting a query of the database from a user, generating a query result including one or more matching patient profiles from the database, and displaying the query result as a correlation medical condition parameters of the user with a medical outcome.

6 Claims, 14 Drawing Sheets

112

402 — Medical condition — ALS ▽
404 — Age range — 35-45
406 — Gender — M ▽

408 — No. of years — 2+

410 — Symptom — Dysphagia ▽

412 — Show predictions — Yes ▽

414 — Treatment — Riluzole ▽

416 — Show dosage — Yes ▽

418 — Side effect — Dizziness ▽

420 — SUBMIT

FIG. 4

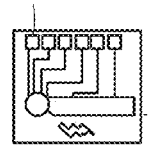
FIG. 13
| | FIG. 13A |
|---|---|
| | FIG. 13B |
PatientsLikeMe
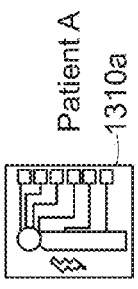
Patient A
1310a
Patient B
1310b
Patient C
1310c
Patient D
1310d
Patient E
1310e
Patient F
1310f
FIG. 13A
| Key Factors | Relative Importance 308 |
|---|---|
| △ Profile | ○ 100 |
| △ Genome | ○ 50 |
| △ Disease | ○ 30 |
| △ Function | ○ 100 |
| △ Interventions | ○ 10 |
| △ Symptoms | ○ 20 |
1306
Patient
1304
1302

PERSONALIZED MANAGEMENT AND COMPARISON OF MEDICAL CONDITION AND OUTCOME BASED ON PROFILES OF COMMUNITY PATIENTS

RELATED APPLICATION

This application is a continuation of U.S. patent application Ser. No. 12/251,031, filed on Oct. 14, 2008, which is a continuation of International Application No. PCT/US08/79673, filed on Oct. 12, 2008, and claims priority to U.S. Provisional Patent Application No. 60/998,669, filed on Oct. 12, 2007, U.S. Provisional Patent Application No. 60/998,768, filed on Oct. 12, 2007, and U.S. Provisional Patent Application No. 61/070,067, filed on Mar. 20, 2008. The entire contents of each of these applications is hereby incorporated by reference herein.

TECHNICAL FIELD

The invention relates to a data processing system and a method for personalized management of medical condition, body function, health, and well-being. More particularly, the invention relates to the entering of personalized data and query parameters for searching profiles of a community of individuals and producing a query result of matching profiles. The invention is further directed toward the viewing and comparing of the matching profiles to better understand and manage a medical condition, body function, health, and well-being.

BACKGROUND OF THE INVENTION

The advent of the World Wide Web offers new opportunities for people to share information, opinions, and experiences on virtually any topic. With the support of web-based systems and methodologies, people with common goals and interests can interact and communicate instantaneously from anywhere on the globe. For example, people can use a computer dating web site to search for a compatible mate. A person can create an account on the web site and enter personal information which is stored in a user profile in a database. The database contains profiles of other persons who use the web site. A person can search for a compatible mate by entering information on characteristics they seek in their mate. The web site can process the search criteria and return a list of matching profiles. The person can then obtain further information and contact a potential mate.

Many web sites exist to serve a particular group of people who share common goals or attributes. For example, U.S. Patent Publication No. 2003/0187683 describes a system for establishing weight control programs. The system allows persons to enter, update, and monitor their weight, and permits users to share recipes and establish meal plans. U.S. Pat. No. 7,029,441 describes a system for comparing non-human animal subjects by animal breed or genetic disposition. For example, laboratory test results for a non-human animal subject can be compared with genetic data for the group.

The existing art includes examples of systems for monitoring patient information to assist in providing medial care. U.S. Pat. No. 6,956,572 describes a system for monitoring patients for critical care. The system includes sliders for setting maximum and minimum thresholds for a particular medical parameter for a patient and the current value for the parameter. This allows the medical staff to quickly determine whether or not a patient's condition is normal. Another example, the LifeLines software from the University of Maryland Human-Computer Interaction Lab of College Park, Md., is a system for visualizing medical history records, which allows medical personnel to examine medical history records in detail. The system includes visual tools such as timelines and icons to denote past events in the medical history.

SUMMARY OF THE INVENTION

The invention provides a method of studying the efficacy of an intervention. The method includes: providing a graphical user interface allowing one or more patients to input information regarding their diseases, symptoms, and remedies; collecting information from a plurality of patients before each of the patients employs a remedy to treat a disease; collecting information about the remedy; collecting information from the plurality of patients after a subset of the patients employs a remedy to treat the disease; and determining the efficacy of the remedy in treating the disease. The method can include comparing the efficacy of the remedy with data from one or more control patients. The step of determining the efficacy of the remedy can include comparing the pre-remedy information with post-remedy information.

The invention also provides a method of identification of a possible personalized intervention for a patient experiencing at least one complication or dissatisfaction with outcomes from a present intervention. The method includes: providing a database containing patient information for a plurality of patients including one or more attributes for each patient in the database; providing a graphical user interface displaying allowing a patient to formulate a request specifying one or more attributes of the patient; searching the database of patient information for patients having the specified one or more attributes including at least one of the specified side effects; and returning one or more alternative interventions that were employed by other patients that experienced the one or more specified side effects when employing the one or more interventions.

The attributes include one or more diseases affecting the patient, one or more interventions employed by patient, and one or more side effects experienced by the patient. The one or more attributes can include at least one selected from the group consisting of: age, race, ethnicity, gender, height, weight, body mass index (BMI), body volume index (BVI), genotype, phenotype, disease, disease severity, disease progression rate, measures of functional ability, quality of life, interventions, and remedies.

The disease can include at least one selected from the group consisting of: neurological diseases, Amyotrophric Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer blood cancer, fibromyalgia, epilepsy, post traumatic stress disorder, traumatic brain injury, cardiovascular disease, osteoporosis, chronic obstructive pulmonary disease, arthritis, allergies, autoimmune diseases, and lupus.

The alternative interventions can be the most recent interventions employed by the other patients.

The invention also provides a method for providing personalized medical information. The method includes: providing a database containing patient information for a plurality of patients including one or more attributes for each patient in the database; providing a graphical user interface displaying one or more attributes of a patient, the graphical user interface allowing the patient to formulate a search request specifying at least one of the attributes; searching the database of patient information for patients having the specified one or more attributes; and returning data to the patient identifying a set of other patients having the specified one or more attributes.

The one or more attributes can include at least one selected from the group consisting of: age, race, ethnicity, gender, height, weight, body mass index (BMI), body volume index (BVI), genotype, phenotype, disease, disease severity, disease progression rate, measures of functional ability, quality of life, interventions, and remedies.

The database can include one or more correlations between an attribute and at least one secondary attribute selected from the group consisting of: quality of life, functional ability, pain, and treatment intensity.

The disease can include at least one selected from the group consisting of: neurological diseases, Amyotrophic Lateral Sclerosis (ALS), Multiple Sclerosis (MS), Parkinson's Disease, Human Immunodeficiency Virus (HIV), Acquired Immune Deficiency Syndrome (AIDS), depression, mood disorders, cancer blood cancer, fibromyalgia, epilepsy, post traumatic stress disorder, traumatic brain injury, cardiovascular disease, osteoporosis, chronic obstructive pulmonary disease, arthritis, allergies, autoimmune diseases, and lupus.

The data returned cam include individual data for one or more members of the set of other patients. The data returned can include aggregate data for one or more members of the set of other patients. The method can include processing a request from the patient to view individual data. The method can include processing a request from the patient to modify a composition of the set of other patients.

The composition of the set of other patients can be defined by fuzzy logic. The step of modifying the composition of the set of other patients can include modifying the range of attributes of patients within the set. The step of modifying the composition of the set of other patients can include modifying the importance of attributes of patients in composing the set. The composition of the set of other patients can be defined by an optimal matching algorithm on a graph of attribute similarity metrics. The composition of the set of other patients can be defined by a scalar-vector decomposition on a matrix of similarities of attributes of the set of other patients. The method can include conducting a multivariate pattern matching search of data related to the other patients.

The invention also provides a computer-readable medium whose contents cause a computer to perform a method for providing personalized medical information. The method includes providing a database containing patient information for a plurality of patients including one or more attributes for each patient in the database; providing a graphical user interface displaying one or more attributes of a patient, the graphical user interface allowing the patient to formulate a search request specifying at least one of the attributes; searching the database of patient information for patients having the specified one or more attributes; and returning data to the patient identifying a set of other patients having the specified one or more attributes.

The invention provides a method for personalized management of medical information and outcome, including the steps of providing a database of patient profiles, each profile including at least one medical condition parameter and at least one medical outcome parameter, providing a user interface for inputting a query of the database from a user, the query being based on at least one medical condition parameter, generating a query result including one or more matching patient profiles from the database, and displaying the query result as a correlation of the medical condition parameter with a medical outcome.

The patient profile can include a plurality of medical condition parameters.

The medical condition parameter can be a disease symptom, a treatment, a treatment reason, a treatment side-effect, a treatment dosage, a diagnosis, a stage of disease, nutritional information, environmental information, activity information, geographic information, genotypic data, phenotypic data, family history data, or a milestone related to the medical condition. The medical condition parameters are associated with a particular disease or conditions (for example, Amyotrophic Lateral Sclerosis, Multiple Sclerosis, Parkinson's Disease, etc.) or combination of diseases or conditions.

The medical outcome parameter can be survival, a disease symptom, a treatment, a treatment reason, a treatment side-effect, a treatment dosage, a diagnosis, a stage of disease, nutritional information, environmental information, activity information, geographic information, genotypic data, phenotypic data, family history data, a milestone related to the medical condition, a medical prediction, or an aggregation of medical condition parameters.

The user interface can be a textual interface, a graphic interface, or a voice-activated interface.

The user can be a patient afflicted with a disease including, but not limited to, neurological diseases (e.g., Amyotrophic Lateral Sclerosis (ALS), Multiple Sclerosis (MS), Parkinson's Disease), Human Immunodeficiency Virus (HIV), Acquired Immune Deficiency Syndrome (AIDS), cancers (e.g. bladder cancer, blood cancer, breast cancer, colorectal cancer, endometrial cancer, leukemia, lung cancer, lymphoma, ovarian cancer, pancreatic cancer, prostate cancer, and skin cancer), diabetes, digestive disorders (e.g. irritable bower syndrome, gastro esophageal reflux disease, Crohn's Disease) depression, anxiety disorders, post traumatic stress disorder, mood disorders, psychotic disorders, personality disorders, and eating disorders.

The method can further include the step of displaying the medical outcome for the times at which the medical outcome was recorded.

The method can further include the step of ranking the matching patient profiles. The step of ranking the matching patient profiles can further include sorting the matching patient profiles based on medical outcome.

The method can further include the step of providing at least one medical prediction of the user's future medical condition. The method can further include the step of assigning a probability to the at least one medical prediction, the probability being how likely the medical prediction is for the user. The probability can be a number between 0 and 100.

The medical prediction of the user's future medical condition can be a prediction of what the medical condition of the user would be at a future date, e.g., one year from the current date.

The method can further include the step of aggregating the medical outcome for one or more patient profiles sharing the medical outcome.

The invention can be directed toward a method for personalized management of medical information and outcome, including the steps of querying a database of patient profiles, each profile comprising at least one medical condition parameter and at least one medical outcome parameter, wherein the query is based on at least one medical condition parameter, and viewing a query result including matching patient profiles from the database, wherein the query result correlates the at least one medical condition parameter of the user with a medical outcome.

The method can further include the step of planning, based on the query result, a treatment method correlated with a desired medical outcome.

The method can further include the step of planning, based on the query result, at least one daily activity correlated with a desired medical outcome.

The invention can be directed toward a computer-readable memory device encoded with a data structure for transferring data between a client program and a server program during a procedure call, the server program including functions for invocation by the client program, the functions including at least one parameter, the data structure including personalized data, the personalized data including patient profiles for a plurality of patients, medical condition measurements for the patients, and at least one medical outcome for a plurality of patients. The personalized data corresponds to the at least one parameter that is transferred from the client program to the server program when one of the functions is invoked.

BRIEF DESCRIPTION OF THE DRAWINGS

FIG. 4 is a diagram a user interface for inputting a user query.

DEFINITIONS

Figure 1:
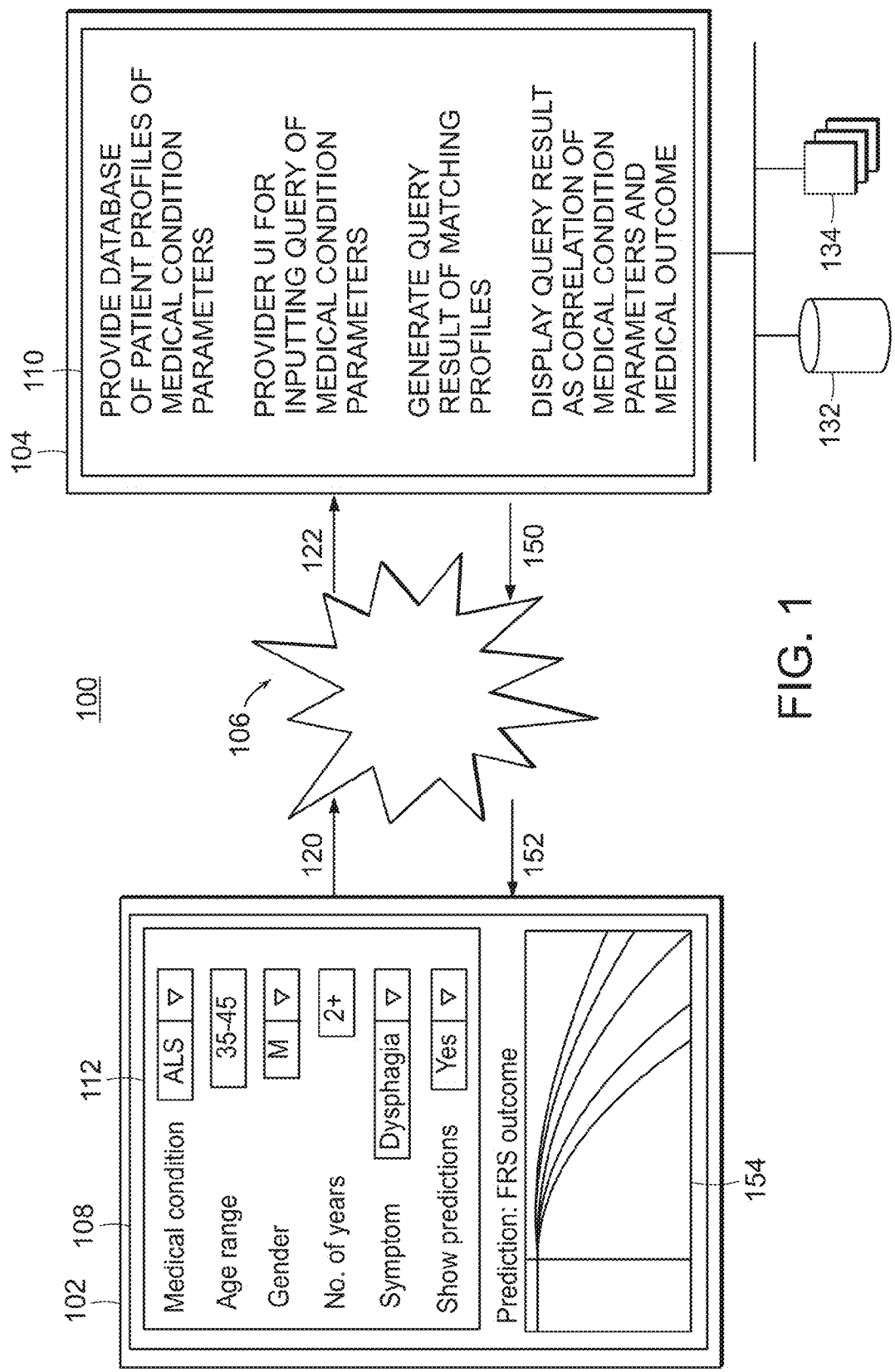
FIG. 1 is a diagram depicting a web-based system and method.

The instant invention is most clearly understood with reference to the following definitions:

As used in the specification and claims, the singular form "a," "an," and "the" include plural references unless the context clearly dictates otherwise.

The term "disease" refers to an abnormal condition of an organism that impairs bodily functions. The term disease includes a variety of physical ailments including, but not limited to, neurological diseases (e.g., Amyotrophic Lateral Sclerosis (ALS), Multiple Sclerosis (MS), Parkinson's Disease), Human Immunodeficiency Virus (HIV), Acquired Immune Deficiency Syndrome (AIDS), cancers (e.g., bladder cancer, blood cancer, breast cancer, colorectal cancer, endometrial cancer, leukemia, lung cancer, lymphoma, ovarian cancer, pancreatic cancer, prostate cancer, and skin cancer), diabetes, digestive disorders (e.g., irritable bower syndrome, gastro esophageal reflux disease, and Crohn's Disease), cardiovascular diseases, osteoporosis, chronic obstructive pulmonary disease (COPD), arthritis, allergies, geriatric diseases, and autoimmune diseases (e.g., lupus). The term disease also include mental ailments including, but not limited to, depression, anxiety disorders, post traumatic stress disorder, mood disorders, psychotic disorders, personality disorders, and eating disorders.

The term "medical condition" refers to a manifestation of a disease such as a symptom. For example, if a patient suffers from Amyotrophic Lateral Sclerosis (ALS), the patient may experience one or more medical conditions such as dysphagia (impaired swallowing).

The term "intervention" refers any event that has a positive, negative, or neutral effect on one or more medical conditions. The term intervention includes a variety of activities including, but not limited to, administration of a medication, administration of a remedy, administration of a nutritional supplement, administration of a vitamin, exercise, physical therapy, massage, stretching, consumption of food, rest, and sleep.

DETAILED DESCRIPTION OF THE INVENTION

The invention is directed toward a method for personalized management and comparison of medical conditions and outcomes based on patient profiles of a community of patients. Patients can find other patients like themselves using, for example, a web-based data processing system to query a database of patient profiles of a community of patients. The query can include, for example, symptomology, medical conditions, diagnoses, treatments, therapies, life style factors, environmental factors, family history, and genetics. For example, a Multiple Sclerosis (MS) patient can find MS patients within the age range of 35-45 who suffer from, for example, relapsing-remitting MS (patients who have unpredictable relapses of MS symptoms, but return to normal between relapses) vs. primary progressive MS (patients who have steadily worsening MS symptoms). The web-based system can return a set of matching profiles from the database of patient profiles. The patient can view the matching profiles and perform further queries. The query can be performed by the patient's doctor, nurse, or medical assistant on behalf of the patient. The query can also be performed by a researcher or a clinician.

The patient can obtain medical outcomes based on entered medical condition parameters. For example, the patient can learn about a treatment for MS by selecting the treatment. The web-based system can return profiles of all MS patients who have taken the treatment, including dosages, frequency, common side effects, and behaviors to help minimize symptoms of the disease. Also, the patient can obtain predictions of how his disease may progress over the next few years, based, in part, on patients in the community with more advanced forms of the disease. For example, an Amyotrophic Lateral Sclerosis (ALS) patient can select an ALS treatment, for example, riluzole. The system can return matching profiles of patients who have taken riluzole and their survival rates. For example, the system may indicate that patients with bulbar-onset of ALS (a form of ALS which first affects the brain stem) who have taken at least 100 mg of riluzole daily lived an average of a few months longer than those who did not take riluzole. Also, the patient may learn that patients with bulbar-onset ALS often suffer from excessive yawning. The patient can thus better assess and manage his disease by comparing himself to other patients in the ALS community.

A web-based data-processing system 100 shown in FIG. 1 can be used to implement a method for practicing the invention. Web-based data-processing systems are well known in the art and can include a client computer 102 and a server computer 104. The client and server computers can be coupled to each other over the Internet 106. Alternatively, the client and server computers can be coupled to each other over an intranet, for example, behind a firewall of a private corporate network. The private corporate network can be the network for a private hospital.

Referring to FIG. 1, the client computer can include a client software program 108 for executing software applications. The client software program 108 can be an Internet browser such as INTERNET EXPLORER®, available from Microsoft Corporation of Redmond, Wash., FIREFOX®, available from the Mozilla Foundation of Mountain View, Calif., or OPERA®, available from Opera Software AS of Oslo, Norway. The Internet browser can display content encoded in a variety of standards such as Hyper Text Markup Language (HTML), and FLASH®, AIR®, and ACROBAT® platforms available from Adobe Systems of San Jose, Calif. User interfaces can include standard web input elements such as text boxes and toggle buttons for entering text and selecting options. The client computer can include input devices, such as a mouse, keyboard, or touch screen for entering information into the user interface.

The client computer need not be a personal computer per se, but rather encompasses devices such as handheld devices, personal digital assistants, and cellular phones. Mobile devices advantageously allow for more frequent data collection as well as well as reminders for patients to engage in an interventions such as consumption of medication. Suitable mobile device can be specifically constructed for the methods described herein or can be existing mobile devices such a smart phones available under the BLACKBERRY® trademark from Research in Motion Limited of Waterloo, Ontario, the PALM® trademark from Palm, Inc. of Sunnyvale, Calif., and the IPHONE™ trademark from Apple, Inc. of Cupertino, Calif.

The user interface can also be a text-based interface. For example, the server can send a text message or an email to a cellular phone or a smart phone asking how the patient is feeling. The patient can respond with an appropriate answer.

Likewise, the user interface can be an audio interface in which the server periodically places a telephone call to the patient asking how the patient is feeling. The patient can respond verbally, which will be then processed according to known voice recognition software.

The server computer can include a server software program 110 including a web server, for example, Apache Server, and an application server, for example, Cold Fusion Application Server. The server computer can include a database server or engine for encoding and storing data such as patient profiles. Suitable database software includes include DB2® and INFORMIX®, both available from IBM Corp. of Armonk, N.Y.; MICROSOFT JET® and MICROSOFT SQL SERVER® both available from the Microsoft Corp. of Redmond, Wash.; MYSQL® available from the MySQL Ltd. Co. of Stockholm, Sweden; ORACLE® Database, available from Oracle Int'l Corp of Redwood City, Calif.; and SYBASE® available from Sybase, Inc. of Dublin, Calif.

The patient profiles can include entries for the personalized data of patients, including, for example, name, age, gender, disease, symptomology, medical condition measurements, diagnoses, treatments, therapies, life style factors, environmental factors, family history, and genetics.

The client software program 108 can be used to display a user interface 112 to enter query parameters including demographic data and medical condition parameters. The query can be submitted to the server software program 120 and the server software program can receive the query 122. The server software program can analyze the data, for example, using function calls executing on a microprocessor. The server software program can generate a query result comprising a set of patient profiles matching the entered query criteria. The server can create an image to display the query result as a correlation of the entered medical condition parameters with a medical outcome. The server can send the image back to the client program 150, which can receive 152 and display the image in a web browser 154. Alternatively, the server can pass the query result as a set of data values, which the client software program can receive and display on the client computer. For example, the client software program can include a custom software plug-in to receive and process the data values, create a display of the correlation, and enable the user to interact with the display.

Medical Condition Parameters

Medical condition parameters are personalized data related to a person's medical condition, body function, health, and well-being. Medical condition parameters can be a disease symptom, such as dysphagia (impaired swallowing) related to a patient diagnosed with ALS, a treatment, such as riluzole for ALS, a treatment reason, such as "to slow the progression of my ALS", treatment dosage, such as 1000 mg per day, a diagnosis, such as the date the disease was diagnosed, a disease type, such as bulbar-onset ALS (ALS beginning in the brain stem), a stage of disease, such as early, mid, or advanced ALS, nutritional data, such as caloric intake of a patient, environmental information, such as exposure to second-hand smoke, activity information, such as daily exercise routines or naps, geographic information, such as an address or town of residence, genotypic data, such as data related to a genetic trait of a patient, or phenotypic data, such as data related to the outer appearance of a patient. Medical condition parameters can also include family history data, for example, history of cancer or other medical problems in the family, or a milestone related to a disease, such as the need for ventilation machines or other equipment to cope with the disease. For example, an ALS patient may require a wheelchair due to loss of leg mobility.

Medical Outcome

A medical outcome is information resulting from the analysis of personalized data, which may include analysis of demographic data and medical condition measurements. Analysis of the data can include producing a set of patient profiles which match entered query criteria. The patient profiles can be stored in a database of patient profiles of a community of patients. A medical outcome can include an averaging of personalized data, for example, an averaging of experienced treatment side-effects for a group of ALS patients. A medical outcome can include a prediction of a patient's future medical condition. A medical outcome can include information relevant to entered medical condition parameters and demographic data. For example, the medical outcome can be a summary of the development of a disease based on the entered disease type. The medical outcome can include survival data. For example, the medical outcome can include relevant data that ALS patients who took riluzole lived an average of 3.5 months longer than ALS patients who did not take riluzole. The medical outcome can include an aggregation of data combined from several data measurements, for example, ALS patients in the community of patients can be aggregated by ALS severity over time to produce a graph of statistical variances of the progression of the disease.

Medical outcomes can include survival, disease symptom, treatment, treatment reason, treatment dosage, diagnosis, stage of disease, nutritional information, environmental information, activity information, geographic information, genotypic data, phenotypic data, family history data, or a milestone related to a medical condition.

Community of Patients

A community of patients can include users with restricted access to the web-based system who have provided one or more personalized data entries stored on the system and related to demographic and medical condition data. Users can assess, track, and manage their medical condition using the web-based system. For example, users can query a database of patient profiles of the community of users to find users or patients like them. The community of patients is comprised of other users of the web-based system who have also entered personalized data for their respective medical condition. A user may better understand his own medical condition by comparing himself to others in the community of patients using the query capability and through other means, such as email and text messaging. A user can communicate with other users and plan treatments and daily activities to help manage his disease. A user can learn about the progression of his disease by viewing patient data from others on the system with more advanced forms of his disease and by viewing medical outcome data correlated with entered query criteria.

Figure 2:
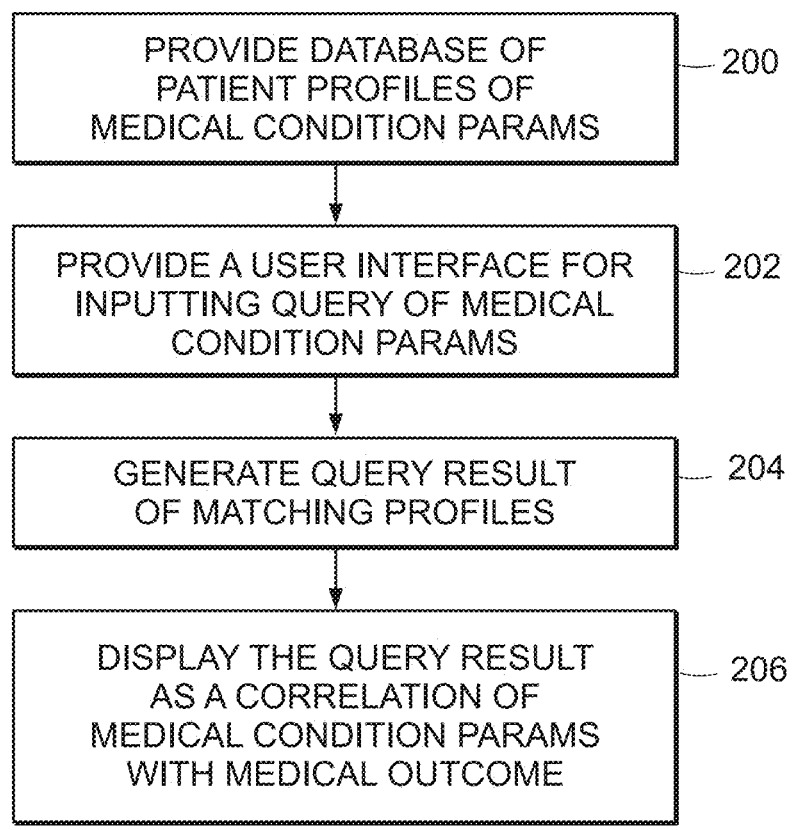
FIG. 2 is a diagram depicting a method for practicing the invention.

As shown in FIG. 2, the invention can be directed to a method including the steps of providing a database of patient profiles 200, providing a user interface for inputting a query of the database from a user 202, generating a query result including one or more matching patient profiles from the database 204, and displaying the query result as a correlation medical condition parameters with a medical outcome 206.

Providing Patient Profiles

Figure 3:
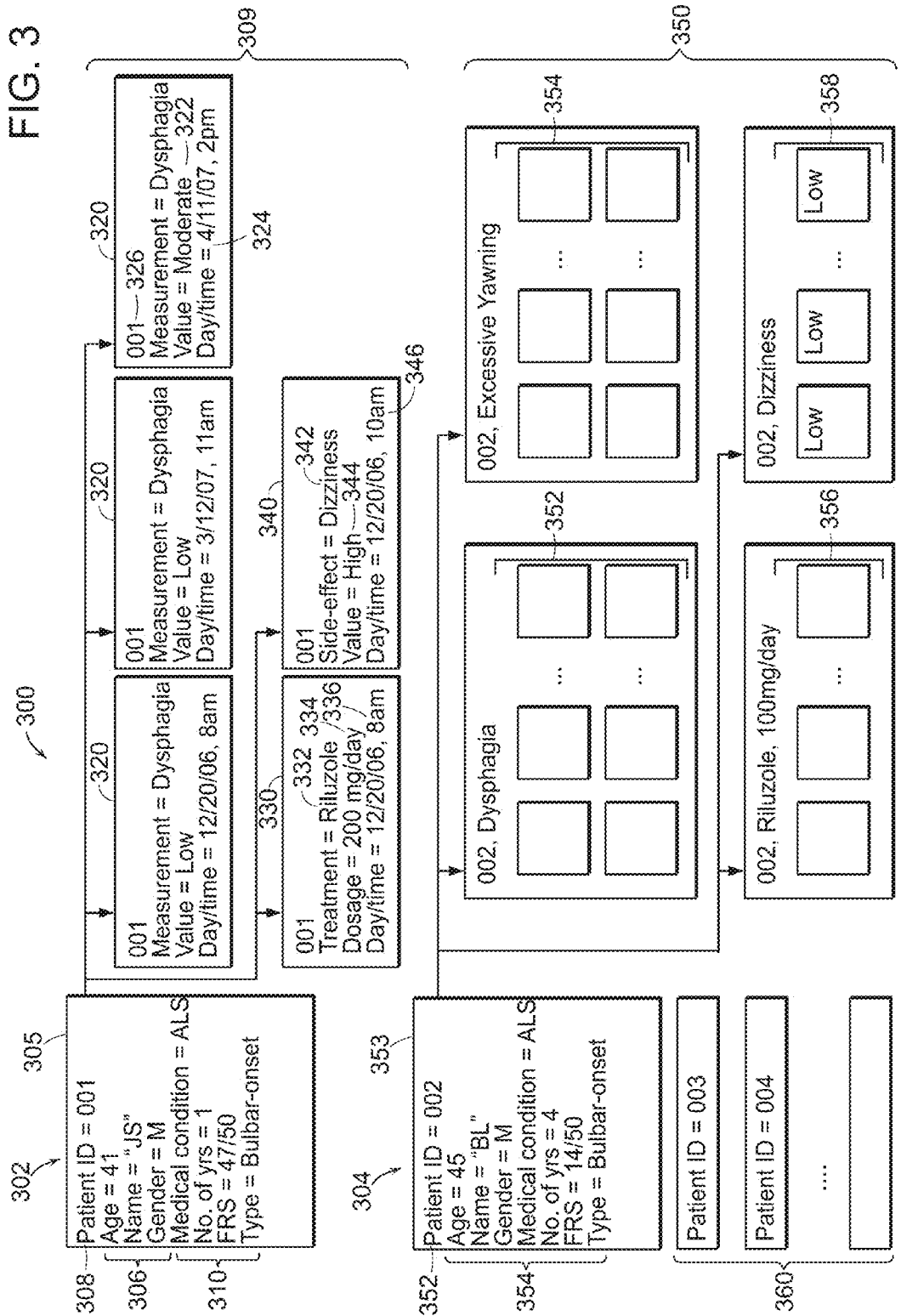
FIG. 3 is a diagram depicting a database of patient profiles of a community of patients.

Referring to FIG. 3, the invention can provide a database of patient profiles 300 of a community of patients, including patient profiles for a user 302 and patient profiles of other users in the community 304. A patient profile can be a database table 305 in a relational database, such as SQL or Oracle, wherein the database table is stored in a memory. For example, demographic data 306 for a user can be stored in a separate database table 305, including the user's name, for example, "JS", age, for example, "41", and gender, for example, "male". Each patient in the community of patients can have a unique patient identifier for cross-referencing database tables 309 storing personalized data for the patient. For example, a user can have the unique patient identifier, "001" (308). The database table 305 can also store medical condition information related to a patient's medical condition 310. For example, the database table 305 can include the name of the patient's medical condition, for example, ALS, the number years the patient has had the condition, for example, 1 year, a rating for the severity of the patient's ALS, for example, 47/50, and other patient information, such as the type of ALS, for example, bulbar-onset ALS.

Different database tables 309 can represent various aspects of a user's medical condition. For example, database tables 320 can store a patient's medical condition measurements for dysphagia (impaired swallowing) related to ALS. The database tables can store measured values taken at certain times of the day. For example, the measured values for dysphagia could be, "Low", indicating minimal impaired swallowing, "Moderate", indicating moderate impaired swallowing, and "High", indicating severe impaired swallowing. Each database table can store a separate measurement for the patient's dysphagia, for example, "Moderate" 322, at a particular time, for example, Apr. 11, 2007 at 2:00 PM (324). The database tables can include the unique patient identifier (326) to cross-reference all tables for a patient. The database tables can also store treatment regimens. For example, database tables 330 can store the patient's treatments for drug riluzole (sold as RILUTEK® by Aventis Pharma SA of Antony, France). The database tables can include the name of the treatment 332, the dosage and frequency 334, and the time of day the treatment was administered to the patient 336. Also, the database tables can store side-effects of the treatment. For example, database tables 340 can store patient-experienced side-effects of riluzole, including dizziness. The database tables can include the name of the side-effect 342, the value, for example, "High" 344, and the time of day the side-effect was experienced, for example, Dec. 20, 2006 at 10:00 AM (346).

The database of patient profiles can include similar database tables 350 for other patients in the community of patients. For example, a patient with unique patient identifier "002" (352) can have a database table 353 for storing his demographic and medical condition information 354, including name, age, gender, medical condition, number of years with the condition, a rating of the severity of the medical condition, and the type of the medical condition. Much of the patient's data can match the data for other patients. For example, the user and patient 002 have ALS and bulbar-onset type ALS. Also, the user and patient 002 have dysphagia, take riluzole, and experience dizziness. The database can include tables 350 for storing patient 002's measured symptoms, including dysphagia 352 and excessive yawning 354, treatments, including riluzole 356, and treatment side-effects, including dizziness 358.

The database can include database tables for storing demographic and medical information for other patients in the community of patients 360. These users can also have ALS and share many of the symptoms, treatments, and side-effects with the user.

Alternatively, the patient profiles can be stored in structured data files.

Providing Query Input User Interface

The invention can provide a user interface similar to that shown in FIG. 4 for entering a query from a query user. The user interface 112 can be formatted in a web-based hypertext markup language (HTML) file providing input elements for entering information in a web page displayed in an Internet browser. The HTML file can be stored on the server computer 104 and transmitted via the Internet 106 to the client computer 102, where it is loaded and displayed in the web page. A query user can enter personalized data, medical condition parameters, and output options to query a database of patient profiles for a community of patients 300, as described above.

A query user can be a patient diagnosed with a disease, for example, ALS. A query user can also be the doctor, nurse, or medical assistant of the patient. A query user can also be a researcher or clinician.

The user interface can include a selection box for selecting a medical condition for the query 402. For example, the query user can be a patient diagnosed with ALS and can select ALS in the selection box to find other ALS patients in the community of patients. The user interface can include a text box for entering an age range and a selection box for choosing a gender to find other ALS patients matching the values. For example, the query user can select males 406 within the age range of 35-45 years of age 404. The query user can select the number of years ALS patients have had the disease, for example, "2+" years 408. The query user can select a symptom of ALS, for example, dysphagia 410 to find ALS patients who have experienced dysphagia and entered data regarding this symptom.

The query user can select other options to query the database of patient profiles. For example, the query user can choose to show predictions 412 for the advancement of his ALS. The predictions can show a range of statistical variances for the advancement of the patient's ALS (see FIG. 8). The prediction can be based on aggregated data for other ALS patients in the community of patients.

The query user can select treatment options, including the treatment name, for example, "Riluzole" 414 (a common ALS treatment), treatment dosage 416, and treatment side-effects, for example, "Dizziness" 418. The query user can submit the query by activating the submit button 420.

The user interface is not limited to the embodiment described above. Other embodiments of the user interface can include a textual interface, for example, a user prompt for entering commands and command options, a voice-activated interface, or a touch-screen interface. The user interface can include user interfaces designed to accommodate patients with limited mobility.

Generating Matching Patient Profiles and Displaying Results

Figure 5:
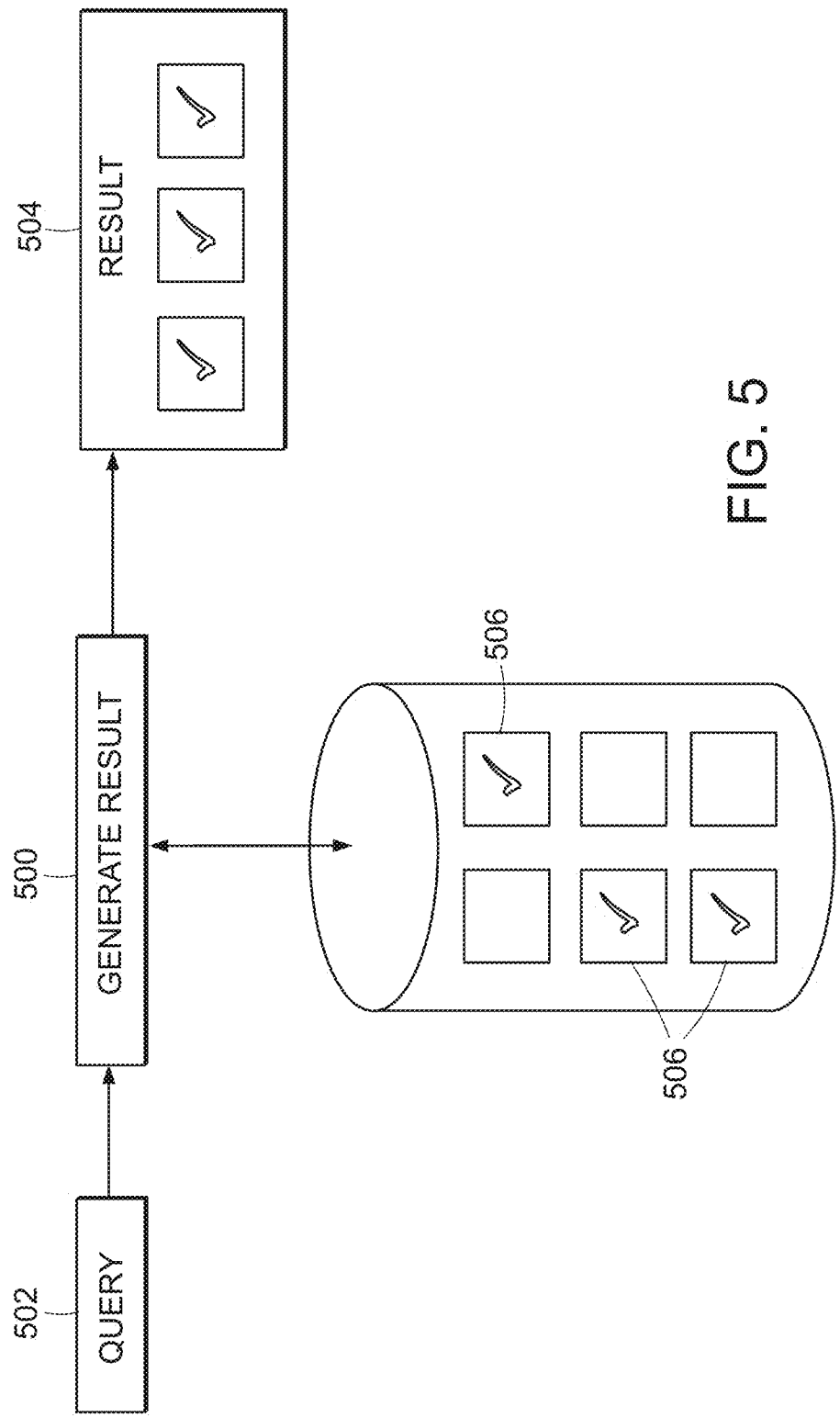
FIG. 5 is a diagram depicting generating a query result of patient profiles matching an entered query.

As shown in FIG. 5, the invention can generate a query result 500 by analyzing a query entered by a user 502. The query result 500 can include a matching set of patient profiles 506 from the database of patient profiles for the community of patients. For example, for the query entered above, the matching patient profiles would include male patients with ALS between the ages of 35-45 who have had ALS for at least 2 years. Furthermore, the matching patient profiles would include patients who have experienced dysphagia, have taken riluzole, and have experienced dizziness as a side-effect of taking riluzole. The query result 504 may also include patient profiles for generating other medical outcomes related to the entered query criteria.

Figure 6:
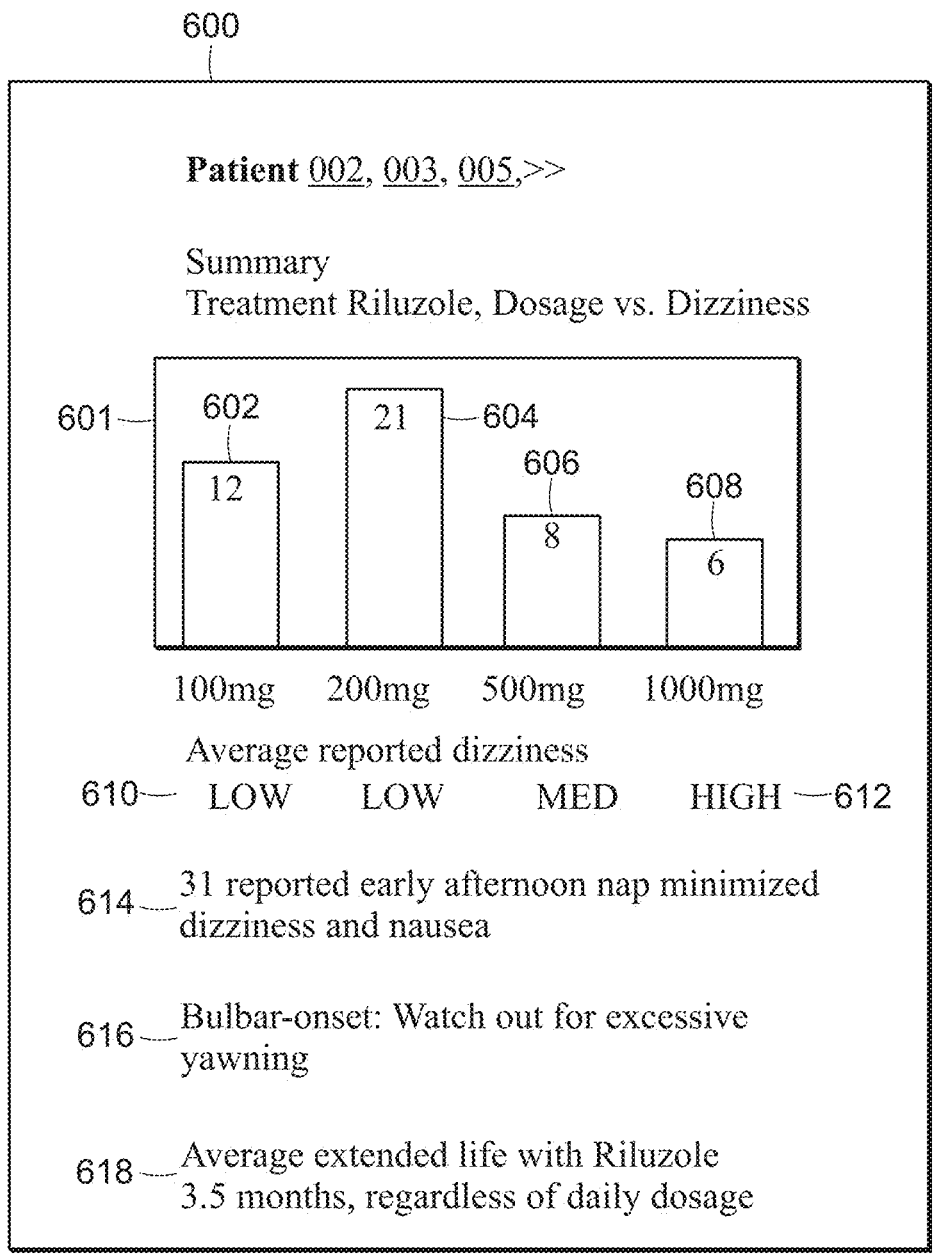
FIG. 6 is a diagram depicting a display of a query result showing a correlation between entered personalized data and medical condition parameters and medical outcomes.

The query result can be displayed as a correlation of the entered medical condition parameters with a medical outcome. As shown in FIG. 6, the display 600 can include a rich variety of information to correlate the entered medical condition parameters and medical outcomes. The display can include aggregate data describing data combined from several measurements. For example, the query result can be displayed as a bar graph 601 aggregating ALS patients who have taken riluzole and their daily dosages. For example, the bar graph can show that 12 ALS patients have taken 100 mg riluzole per day 602, 21 ALS patients have taken 200 mg of riluzole per day 604, 8 ALS patients have taken 500 mg of riluzole per day 606, and 6 ALS patients have taken 1000 mg of riluzole per day 608. Furthermore, medical condition parameters, treatments and treatment dosages can be correlated with medical outcomes, such as treatment side-effects. For example, ALS patients who have taken 100 mg of riluzole per day have experienced on average a low degree of dizziness as a side-effect of riluzole 610. In contrast, ALS patients who have taken 1000 mg of riluzole per day have experienced on average a high degree of dizziness as a side-effect of riluzole 612.

The display of the query result can also include other relevant medical outcomes correlated to the entered query. For example, the display can show that 31 of ALS patients who have taken riluzole report that an early afternoon nap helps minimize dizziness and nausea caused by riluzole 614. The display can include important information related to the patient's ALS, namely, bulbar-onset ALS. For example, the display can show that the patient should be prepared for excessive yawning 616, a symptom common to ALS patients with bulbar-onset ALS. The display can include survival outcome data for ALS patients who have taken riluzole. For example, the display can show that riluzole extends ALS patient survival by 3.5 months, and that the daily dosage did not affect the survival outcome 618.

Generating the query results can further include a query engine that is adaptive to user behavior such that the query results can be personalized to each query user. For example, the query engine can collect, store, and analyze a query user's history of queries. The history of queries may be saved in a query log file. The query engine can also track how a query user has reacted to prior query results. Based on this information, the query engine can tailor individual queries, for example, by adding query parameters, restricting or locking-in certain parameters, etc., before the query is processed. The query engine can also create and leverage user profiles and patterns of similar users to further tailor queries. The query user can rank the appropriateness or usefulness of each piece of returned information, which can be used to further tailor query results.

Medical Predictions and Aggregating Results

Figure 8:
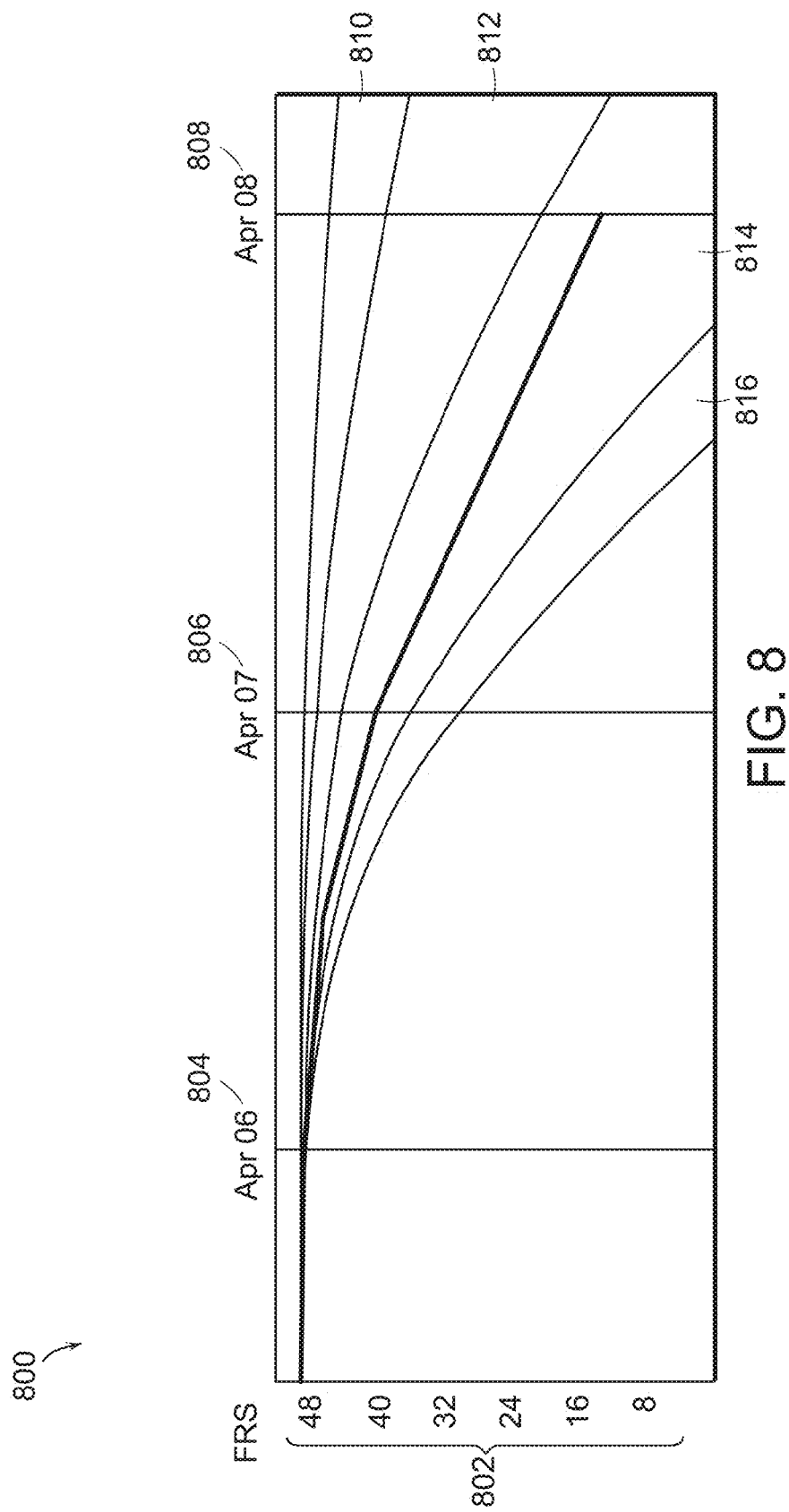
FIG. 8 is a diagram depicting a medical prediction outcome.

The display of the query result can include medical outcome predictions 800, as shown in FIG. 8. For example, a survey of questions can be used to assess and rate the severity of a patient's ALS. The survey of questions can be questions related to the mobility of the patient's appendages and other mobility factors, such as swallowing and breathing. As shown on FIG. 8, the patient's answers can be combined to derive a Functional Rating Scale (FRS) score displayed on the vertical axis of the graph 802. The FRS score can be a number between 50 and 0. A FRS score of 50 can represent normal mobility, and a FRS score of 0 can represent complete paralysis or death caused by ALS. The patient's FRS score can be displayed at plurality of score dates, for example, at the time of diagnosis in April of 2006 (804), and at a current date, for example, April 2007 (806). A line can show the predicted progression of the query user's ALS, showing future predictions of what the FRS score could be at future dates, for example, at April 2008 (808).

The medical prediction can include aggregated FRS score data for ALS patients in the community of patients matching the query criteria, for example, males between the ages of 35 and 45 with bulbar-onset ALS. The prediction can show statistical variances of the FRS scores, including the $100^{th}$-$75^{th}$ percentiles 810, $75^{th}$-$50^{th}$ percentiles 812, $50^{th}$-$25^{th}$ percentiles 814, and $0^{th}$-$25^{th}$ percentiles 816. The prediction can include future predictions of what the percentiles could be at future dates.

Graphical Element

Figure 7B:
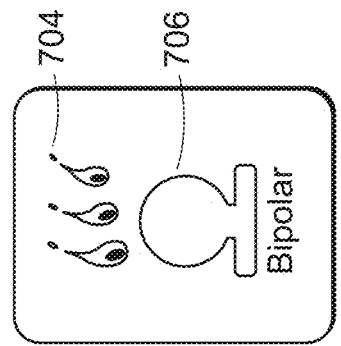
FIG. 7B is an example of a representation of a graphical element including a representation of a patient's medical condition status (in this case, a flare-up of extreme irritability of a patient diagnosed with bipolar disorder).
Figure 7A:
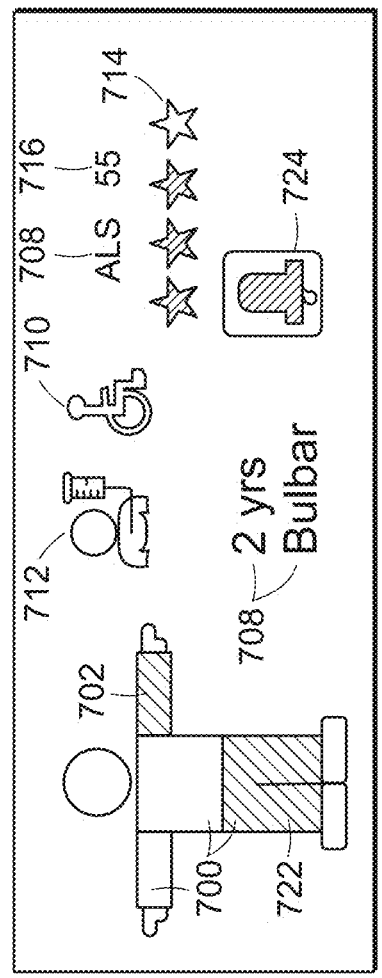
FIG. 7A is an example of a representation of a graphical element showing the data (in this case, a representation of a human, for example, a stickman figure) showing various embodiments of the system.

The display of the query result can include a graphical element representing a plurality of personalized data related to disease, disease symptoms, disease stage, disease status, body function metrics, or life-changing illness. The graphical element includes a representation of an animal body having at least one animal body part. For example, the graphical element can be a stickman figure representing a plurality of human body parts 700, as shown in FIG. 7A. The stickman figure can represent a patient's ALS and its effect on various parts of the patient's body. The stickman can be generated from the query result of matching patient profiles. In one embodiment, the display of the query result includes a stickman figure generated for each matching patient profile.

The animal body parts can include one or more display characteristic, such as a color or a pattern. The color can denote the effect of a medical condition on a body part. For example, green can denote mild onset of symptoms, yellow can denote moderate onset of symptoms, and red can denote severe onset of symptoms. For example, the stickman figure's left arm 702 and legs 722 can be colored red to denote loss of left arm and leg control. In another example shown in FIG. 7B, the body part can be a circular figure representing the head of patient diagnosed with clinical depression, the head drawn blue to denote extreme depression.

The graphical element can include a representation of a patient's medical condition status. For example, a cancer patient in remission can be represented by an "R" displayed next to the stickman figure. A medical condition status can be a flare-up of the patient's medical condition. For example, as shown in FIG. 7B, a patient diagnosed with Bipolar Disorder, a brain disorder that causes unusual shifts in a person's mood, energy, and ability to function, can have a flare-up of extreme irritability represented by flames 704 drawn on top of a circular FIG. 706 representing the patient's head. Alternatively, an emergency situation, such as a broken bone due to a fall can be displayed using an alarm bell icon 724.

The graphical element can include textual information 708 related to a patient's medical condition. For example, the textual information can include the name of the patient's disease, for example, "ALS", a characteristic of the disease, for example, "Bulbar" (bulbar-onset ALS initially affects a certain area in the brain stem), and the number of years the patient has had ALS, for example, "2 yrs."

Disease progression can be divided into milestones. For example, in the early stages of ALS, patients may require a wheelchair after losing mobility in their arms and legs. As the disease advances, patients may lose other voluntary functions, for example, the ability to swallow. Advanced ALS patients may lose the ability to breath on their own, and require special breathing assistance devices, including intermittent positive pressure ventilation (IPPV) or bilevel positive airway pressure (BIPAP) devices. The graphical element can include a representation of at least one milestone related to the patient's medical condition. For example, a wheelchair icon 710 can be used to denote the loss of mobility the patient's legs. A breathing apparatus icon 712 can be added to the graphical element to denote a IPPV or a BIPAP device.

In another example, the milestone can be a session of a cancer patient's chemotherapy, represented by a number denoting the session, for example, "$1^{st}$", "$2^{nd}$", or "$3^{rd}$". Similarly, the milestone can be represented by one or more stars 714. The stars can have a color. In a further example, the milestone can be a number 716 representing a level on the aforementioned Functional Ratings Scale (FRS) for tracking ALS symptoms. The number can represent a Forced Vital Capacity score for measuring an ALS patient's lung strength.

Ranking Matching Profiles

The matching profiles can be ranked, for example, by favorable outcome. For example, query criteria can include treatment, treatment dosage, and side-effect to determine whether dosage has an effect on the side-effect. For example, riluzole taken at 1000 mg per dosage can cause patients to experience more dizziness than riluzole taken at 500 mg per day dosage. The ranked profiles can be sorted based on medical outcome.

Users

Figure 9:
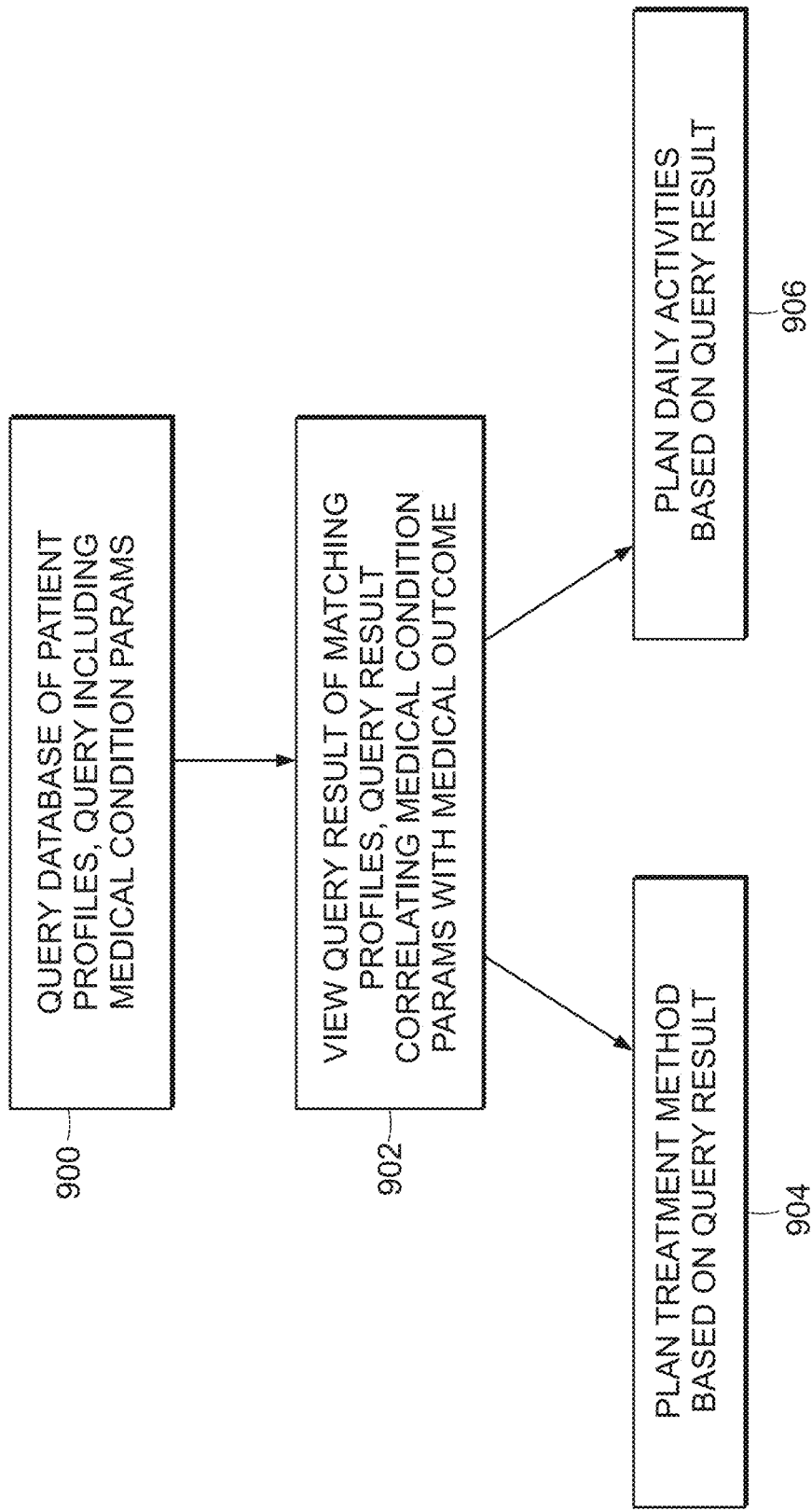
FIG. 9 is a diagram depicting a method of practicing the invention by a user.

As shown in FIG. 9, the invention can be directed toward a method for querying a database of patient profiles for a community of patients 900, the query including medical condition parameters of a user, and viewing a query result of matching patient profiles from the database 902. The query result can correlate a medical condition parameter with a medical outcome, as described above and shown in FIGS. 6, 7A, 7B, and 8.

The method can be practiced by a query user. The query user can be a patient diagnosed with a disease, for example, ALS. The query user can also be a doctor or a nurse of a patient diagnosed with a disease. The query user can also be a clinician or a researcher who enters a query to mine the database of patient profiles for relevant disease information. For example, the researcher can enter a query to find ALS patients experiencing excessive yawning. The researcher can view the query result and determine that many of the ALS patients who reported excessive yawning had bulbar-onset type ALS.

The query user can plan a treatment method based on the query result 904. For example, based on the query result shown in FIG. 6, an ALS patient (or his doctor or nurse) can notice that ALS patients who have taken 1000 mg of riluzole per day generally reported a high degree of dizziness 612. He may also notice that all patients taking riluzole lived in average of 3.5 more months than patients who did not take riluzole, regardless of the dosage frequency 618. Based on this query result, the ALS patient can plan to take 100 mg or 200 mg of riluzole per day as opposed to 1000 mg of riluzole per day to minimize side-effects 610. Alternatively, the patient's doctor, nurse, or medical assistant may recommend the plan to the patient.

The query user can plan a daily activities based on a query result 906. For example, the ALS patient may notice that 31 ALS patients reported (and perhaps recommended) that taking an early afternoon nap minimized dizziness and nausea experienced from taking riluzole 614. Thus, the ALS patient may plan to take a nap in the early afternoon to help mitigate the side-effects of the riluzole.

Adding Medical Condition Parameters

Users can add medical condition parameters to track with the system. For example, a patient diagnosed with ALS may experience excessive, uncontrollable yawning, a symptom of ALS not yet recorded and stored in the database. The user can add the symptom and begin recording measurements of the symptom. Other users in the community of patients may follow suit and record their own measurements of excessive yawning. In this way, patients can benefit from new, flexible ways of recording and tracking their disease and share information about their disease throughout the community.

Data Structure

In one aspect, the invention can be directed toward a computer-readable memory device for encoding a data structure. As shown in FIG. 3, the data structure can include personalized data, including demographic and medical condition data, for a community of users. For example, the person's name, age, gender, age, and a medical condition of the person, such as ALS. The person can have a unique identifier stored in the data structure.

The data structure can be used to transfer stored data values from a memory located on a server computer to a client computer to execute functions of a client software program. Alternatively, the client software computer can transfer entered values, such as medical condition measurements, to the server computer. The server computer can store the entered values in the data structure. The computer-readable memory device can be physically shipped with a software program.

Additional User Interface Embodiments

Figure 10:
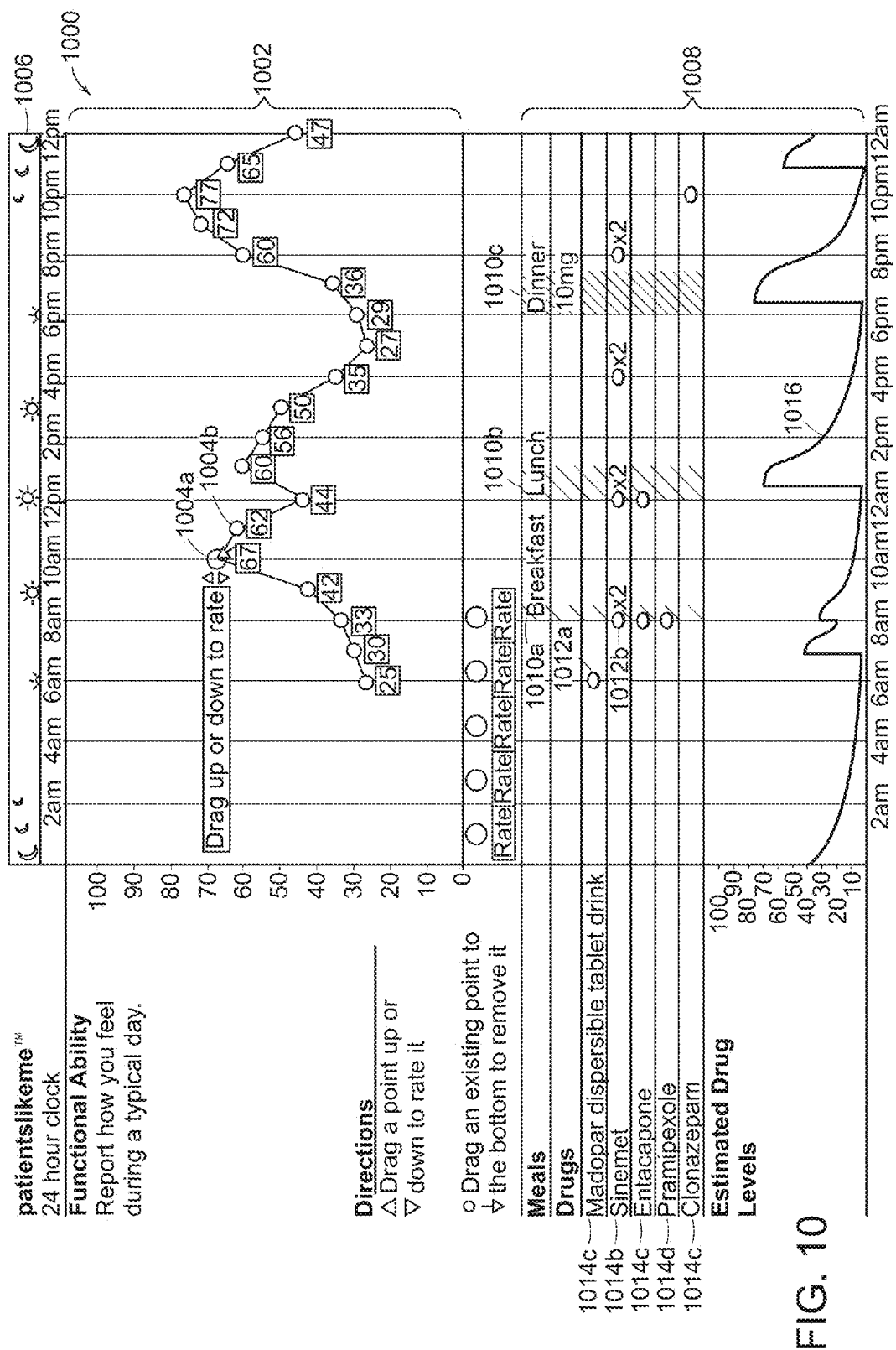
FIG. 10 is a diagram depicting an exemplary user interface for entering patient data.

Referring now to FIG. 10, another exemplary user interface 1000 is provided. Although user interface 1000 is customized for a patient suffering from Parkinson's disease, the principles explained and depicted herein are equally applicable to any disease.

User interface 1000 includes a medical condition metric portion 1002, which allows the patient to input a medical condition metric (in this example, the patient's functional ability). The user can place multiple data points 1004 in the medical condition metric chart, which includes a time scale. Data points 1004 can be adjusted with respect to time and/or magnitude. For example, if the patient is indicating how she feels now or at a designated time, the patient can be limited to moving data point 1004 up or down. Alternatively, the patient can input data for a time by dragging the data point to the left or right. The patient can be restricted in some embodiments from setting a data point in the future.

User interface 1000 also includes an intervention portion 1008. Intervention portion 1008 allows the patient to record one or more interventions such as administration of a medication, administration of a remedy, administration of a nutritional supplement, administration of a vitamin, exercise, physical therapy, massage, stretching, consumption of food, rest, and sleep. For example, the patient can designate when meals are eaten by adjusting bars 1010a, 1010b, 1010c to indicate the beginning and ending of the meal. Likewise, the patient can indicate when one or more drugs 1014a-1014e are administered by placing markers 1012 (which may depict pills) on a time scale.

Various types of remedies can be scheduled for specific times. For example, the patient can be prescribed to take madopar at 6 A.M. In this situation, user interface 1000 can display a medication schedule. The patient can modify this schedule to reflect the actually administration by dragging marker 1012a. Likewise, the patient can indicate that the drug was consumed by clicking on the marker 1012a. Clicking on the marker can change the appearance of the marker 1012a (e.g., its color) and thus can be used by patients, particularly patients with memory problems, to more faithfully follow a medication program.

User interface 1000 can also include pharmacokinetic data, such a pharmacokinetic curve 1016 that depicts the concentration of a medication within the patient over time. Multiple pharmacokinetic curves 1016 can be depicted in various colors or patterns to reflect varying pharmacokinetic properties of various medications.

Patient-Initiated Clinical Trials

The invention enables a community of patients to initiate clinical trials that can be conducted at a lower cost, while still reaching more patients. As discussed herein, patients can input information regarding their diseases, symptoms, and remedies through a graphical user interfaces. This data forms a baseline data set for comparison with data during a clinical trial.

A clinical trial can be initiated by one or more patients, a researcher, an administrator, or other person or organization. The clinical trial can test the efficacy of any intervention such a medication. If the intervention is a prescription medication, patients in the community may need to obtain the medical from their doctor, e.g., through an off-label prescription. Other interventions can be tested without the legal requirement of a physician.

Figure 11:
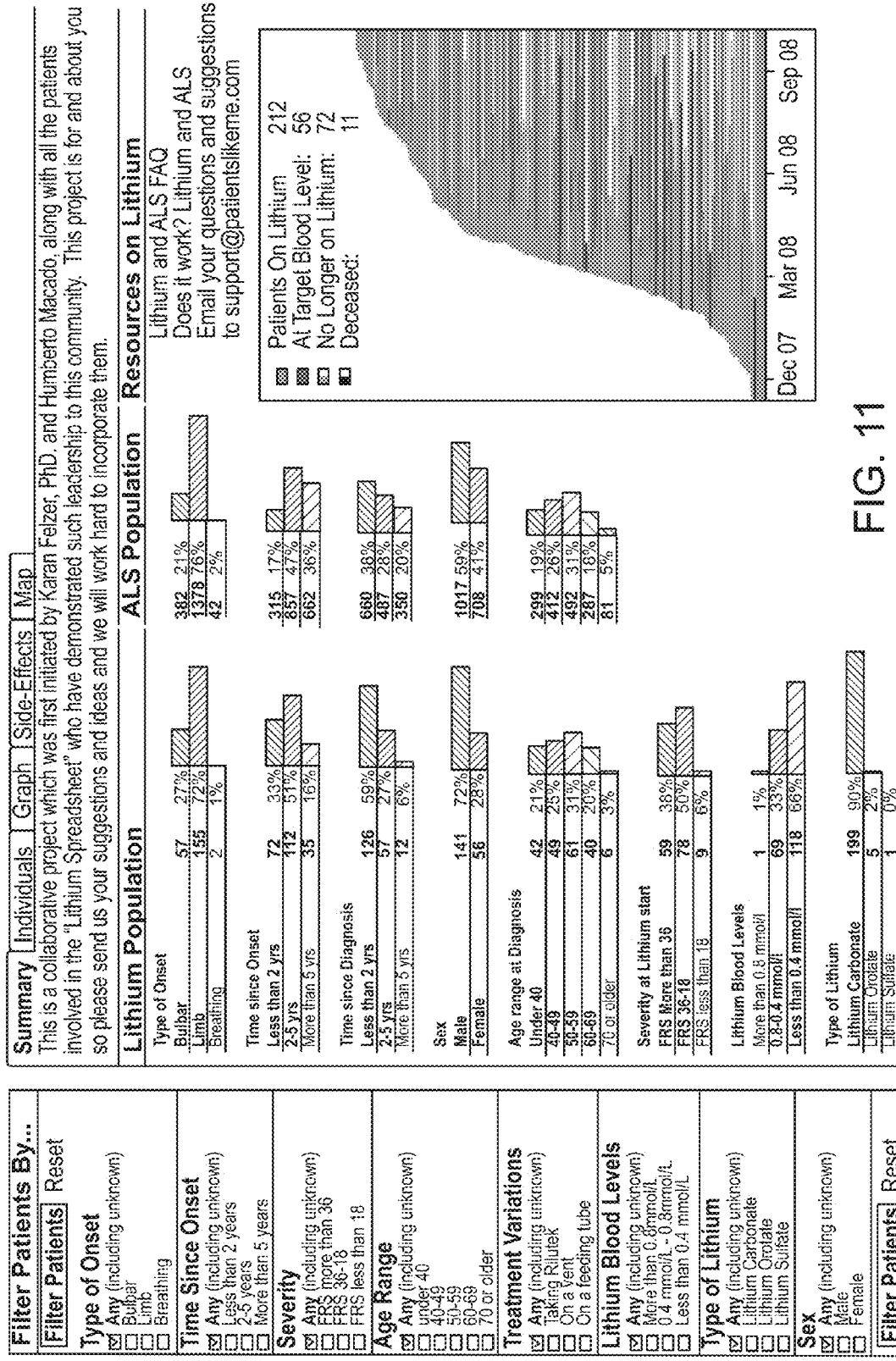
FIG. 11 is a diagram depicting an exemplary user interface for filtering clinical trial data.

As patients begin the intervention, data about the intervention is entered into the graphical user interface and is recorded in the system. This data can be viewed by other patients and easily aggregated as depicted in FIG. 11. The data can be compared with pre-intervention data and data for patients that are not employing the intervention to determine the efficacy of the intervention in accordance with known statistical tools and methods.

Intervention Change Analysis

Pharmaceuticals and other interventions interact with various patients in different ways. A first patient may tolerate an intervention with little or no side effects, while another patient may experience severe side effects that impact the patients health and/or quality of life. Moreover, side effects currently cannot be predicted with a degree of specificity or particularity so that a patient can choose a remedy that will produce minimal side effects. Accordingly, patients frequently try several interventions before finding an intervention with an acceptable level of side effects.

In addition to side effects, patients may be unsatisfied with the effect of an intervention. This is particularly true with antidepressants, where a common practice involves switching antidepressants in the desired response is not achieved within six to eight weeks.

The invention enables patients to shorten the process of choosing a suitable intervention by harnessing the experiences of other patients. As discussed herein, patients input a variety of information about various interventions. This intervention information can include information about an intervention including a name (trademark or generic), a dosage, a frequency, a duration, a patient rating, side effects, and the like.

This information can be stored in a database for later processing. The information can be analyzed for changes. For example, a depressive individual may first be prescribed PROZAC® (fluoxetine hydrochloride). After six weeks, the patient may cease taking PROZAC®, and begin taking WELLBUTRIN® (buproprion). The patient again switch medications and begin taking PAXIL® (paroxetine). The patient may experience the desired effect and continue taking PAXIL® for an extended period of time. The patient may also give high ratings to PAXIL® to reflect his satisfaction with the medication.

Figure 12:
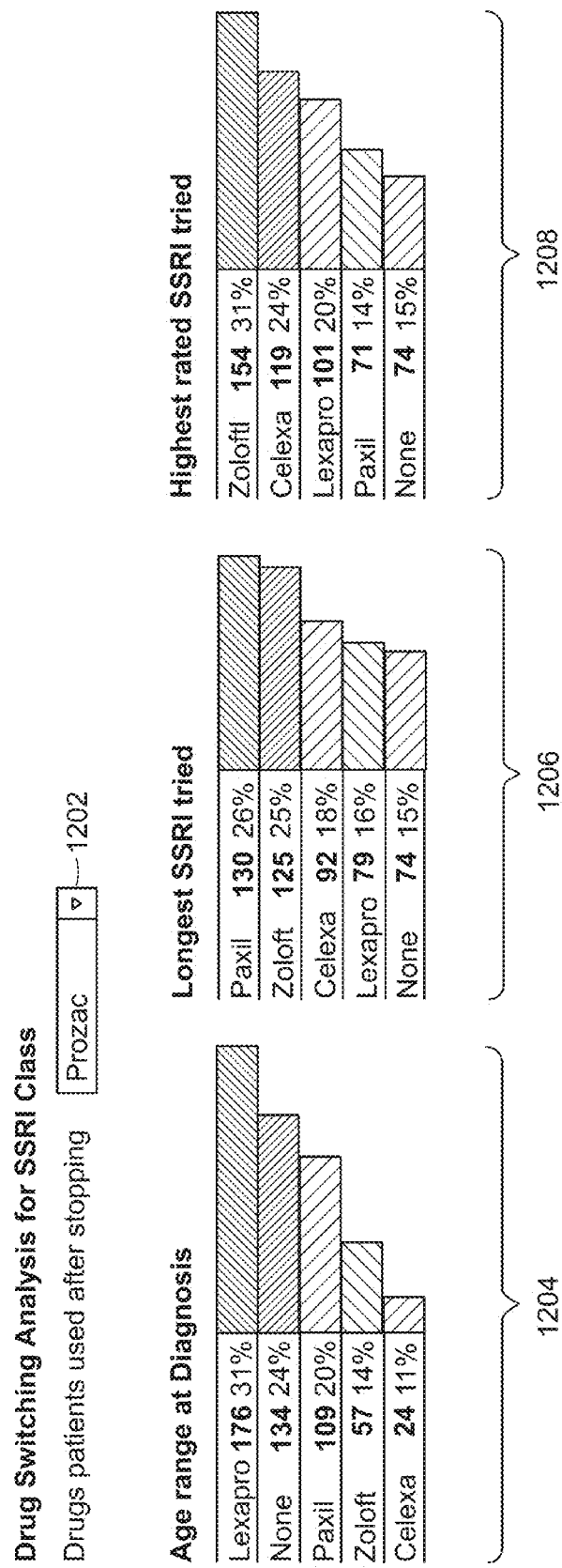
FIG. 12 is a diagram depicting an exemplary user interface for viewing interventions employed by other patients that once employed a particular intervention.

This information is stored in a database, e.g., in a state model. The data can then be mined for relationships between medications. For example, as depicted in FIG. 12, a patient can that is dissatisfied with PROZAC® can request information about other antidepressants taken by other patients in the community. The patient can select PROZAC® using a GUI widget, e.g., drop-down list 1202. One or more graphical elements 1204, 1206, 1208 display population information about antidepressants. For example, graphical element 1204 displays the most recent SSRI (selective serotonin reuptake inhibitor) taken by a group of patients. The patient can see that 31% of patients who took PROZAC® at one point in their treatment are now taking LEXAPRO® (escitalopram). This allows the patient to skip the intervening drugs that many patients have unsuccessfully tried. Likewise, the patient can view the SSRI taken for the longest duration by group of patients (1206) or the highest rated SSRI (1208).

These feature are particularly powerful when combined with the filtering ability described herein. By using the filter feature, a patient can view what SSRI most Caucasian patients who initially took PROZAC® eventually settled on. This filtering can be further refined, e.g., by filtering by genotype. Additionally, the invention can utilize side effects to filter data. For example, a patient that experiences erectile dysfunction while taking an antidepressant can view subsequent antidepressants taken by other patients that experienced erectile dysfunction while taking the same antidepressant.

Community Searching

Figure 13B:
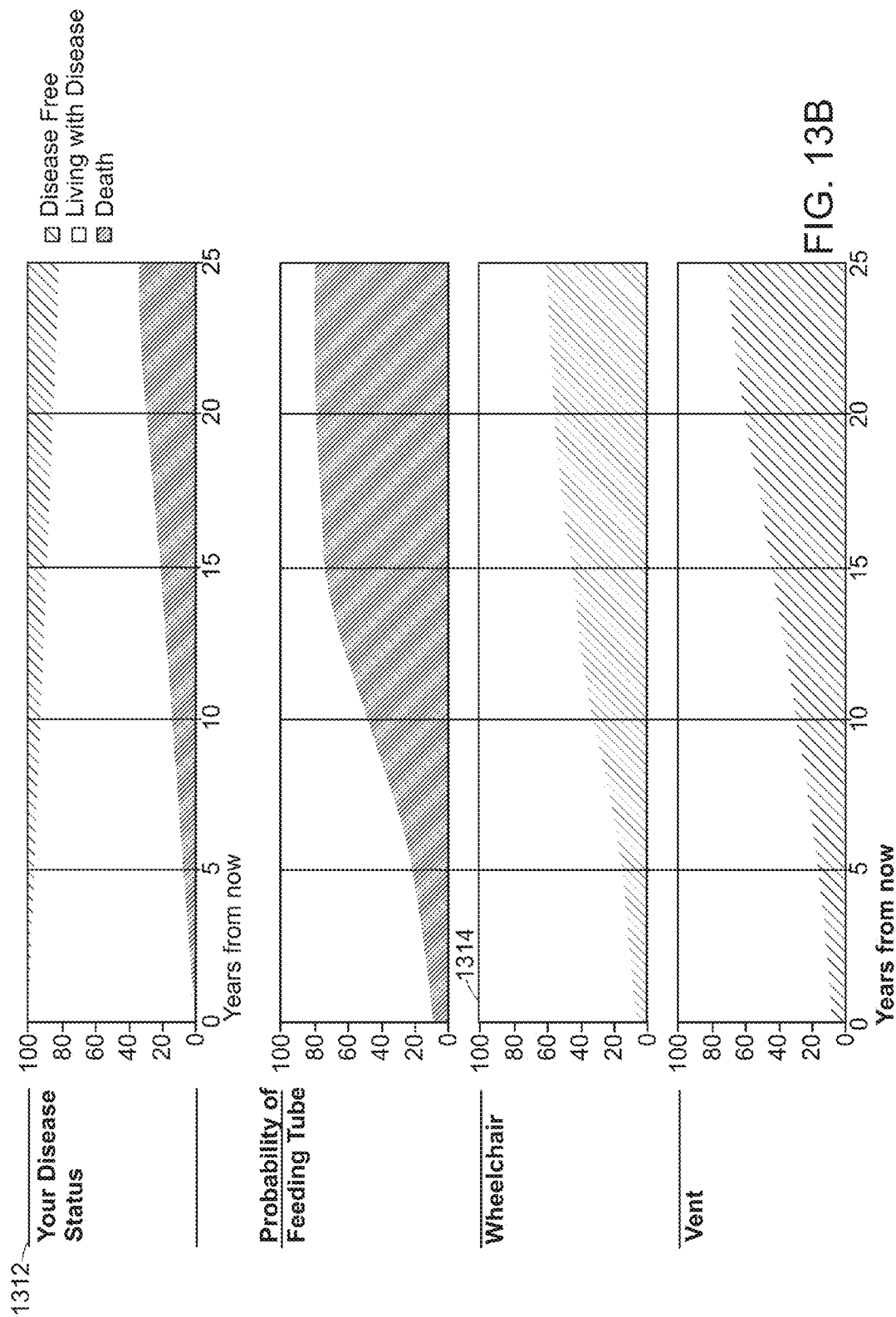
FIG. 13 is a diagram depicting an exemplary user interface for viewing and refining a group of similar patients and prediction of disease progression.

Referring to FIG. 13, an exemplary user interface 1300 is provided for viewing and refining a prediction of disease progression. An icon 1302 represents the patient controlling the system. The icon 1302 includes several color-coded boxes 1304, which represent the status of various body systems or regions (e.g., the legs, the spine, and the eyes).

The user interface 1300 also includes a population chooser interface 1306 for refining the prediction by expanding or contracting the population on which the prediction is made. For example, a patient can initially view a prediction based on all patients within a community (e.g. all patients with ALS). The patient can then alter one or more parameters such as age, gender, race, ethnicity, genotype, etc. The predictions can be updated in real time as the population is altered. In the depicted example, the user can alter the population by sliding one or more sliders 1308 to adjust the relative importance a factor such as profile (e.g., age, gender, race, ethnicity, socio-economic status), genome, disease, function (e.g., as assessed by the ALSFRS-R scale), interventions (e.g., medications consumed), and symptoms (e.g., dysphagia).

The user interface 1300 can display icons 1310a-1310f for one or more patients that are similar to the patient. Icons 1310 can be updated as the patient alters the population using population chooser interface 1306. The patient can "drill down" to view specific details and profiles of one or more patients, for example, by clicking on one of the icons 1310.

The user interface 1300 can also include one or more charts 1212, 1314 depicting predictions of the progression of the patient's disease. Chart 1312 depicts the probability of the patient either (i) recovering from the disease, (ii) living with the disease, or (iii) dying over a twenty-five year period. Chart 314 predicts the probability of the patient requiring assistive devices such as a feeding tube, a wheelchair, or a ventilator over the next twenty-five years.

The user interface can include a graphical element (not shown) that depicts the reliability of the prediction. For example, the graphical element can be modelled after traffic light. A red light can indicate that the prediction lacks a certain level of statistical significance. A yellow light can indicate that the prediction has an intermediate level of statistical significance. A green light can indicate that the prediction has an acceptable level of statistical significance.

The invention can also compute the effect of various stochastic and probabilistic events. For example, the invention can display two different predictions. The first prediction displays the progression of the patient's disease if the patient develops pneumonia; the second prediction displays the progression of the patient's disease if the patient does not develop pneumonia. The invention can also display advice on preventing pneumonia.

The invention can also incorporate the probability of such events into the predictive model. This can be accomplished, e.g., through the use of swarm or multiple agent simulation based on known state transition probabilities, as expressed in Markov chains. Sample measurements can then be taken at arbitrary points in time to determine probabilities of outcomes based on certain criteria. Such criteria can be controllable (e.g., receiving a certain intervention) or uncontrollable (e.g., developing pneumonia).

Additionally, the invention can simulate the effect of earlier actions that were either taken or not taken. For example, a patient can display the predicted disease progression for colon cancer if the cancer was detected two years earlier. Such a simulation can have a powerful effect on the patient's friends and family.

Application to Depression

Some modern theories of depression posit that depression results from cognitive distortions. While all individuals become sad or upset at some points in time, most individuals have the perspective to recognize that such feeling are short-lived. However, individuals with a major depressive disorder are thought by some to lack the ability to recognize recall a time before they entered a depressive episode, and therefore cannot anticipate better times in the future.

The invention described herein are capable of helping persons dealing with depression. Depressed persons can enter their mood or other medical condition metrics into the systems described herein and retrieve graphical representations of these metrics over time. Such a system provides external memory and perspective for the patient.

Furthermore, the inventions described herein can be used by generally healthy individuals in advance of disease. For example, military personnel can record medical condition metrics before deployment to an armed conflict. Such prior medical condition metrics can serve both as a reference point for the military personnel when coping with conditions such a post traumatic stress disorder (PTSD) and to military health personnel seeking to screen for PTSD.

The functions of several elements can, in alternative embodiments, be carried out by fewer elements, or a single element. Similarly, any functional element can perform fewer, or different, operations than those described with respect to the illustrated embodiment. Also, functional elements (e.g., modules, databases, computers, clients, servers, and the like) shown as distinct for purposes of illustration can be incorporated within other functional elements, separated in different hardware or distributed in a particular implementation.

While certain embodiments according to the invention have been described, the invention is not limited to just the described embodiments. Various changes and/or modifications can be made to any of the described embodiments without departing from the spirit or scope of the invention. Also, various combinations of elements, steps, features, and/or aspects of the described embodiments are possible and contemplated even if such combinations are not expressly identified herein

INCORPORATION BY REFERENCE

All patents, published patent applications, and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Specifically, although this application periodically discusses the application of the invention to "diseases", the invention is equally applicable to other medical events such as aging, fertility, and the like. Such equivalents are intended to be encompassed by the following claims.

What is claimed is:

1. A method of facilitating a user-initiated clinical study to determine the efficacy of an intervention, the method comprising:
   providing a graphical user interface on a client computer, the graphical user interface allowing one or more patients within a community of patients to input information regarding diseases of the one or more patients, interventions employed by the one or more patients to treat the diseases, and symptoms experienced by the one or more patients before and after the interventions are employed;

receiving a request from a user to initiate the clinical study to determine the efficacy of the intervention;

collecting information, on a server computer, regarding a disease of the one or more patients and a particular intervention employed by the one or more patients to treat the disease, the information having been input by the one or more patients via the graphical user interface on the client computer;

collecting information, on the server computer, regarding symptoms experienced by the one or more patients before the particular intervention is employed by the one or more patients to treat the disease, the information having been input by the one or more patients via the graphical user interface on the client computer;

collecting information, on the server computer, regarding symptoms experienced by the one or more patients after the particular intervention was employed by the one or more patients to treat the disease, the information having been input by the one or more patients via the graphical user interface on the client computer; and analyzing the information regarding the disease of the one or more patients, the particular intervention employed by the one or more patients to treat the disease, and the symptoms experienced by the one or more patients before and after the particular intervention is employed to determine the efficacy of the particular intervention in treating the disease.

2. The method of claim 1, wherein the analyzing step includes comparing the efficacy of the particular intervention with data from one or more control patients within the community of patients on the server computer.

3. The method of claim 1, further comprising:
conducting a multivariate pattern matching search of data related to patients other than the one or more patients.

4. The method of claim 1, wherein the particular intervention is selected from the group consisting of: administration of a medication, administration of a remedy, administration of a nutritional supplement, administration of a vitamin, exercise, physical therapy, massage, stretching, consumption of food, rest, sleep, and a modification of any of the foregoing.

5. The method of claim 1, wherein the analyzing step includes utilizing data collected from the community of patients prior to the clinical study as a baseline for comparison with the information collected after the one or more patients employ the particular intervention to treat the disease, wherein the data collected from the community of patients is directed to an intervention employed by patients to treat the disease other than the particular intervention.

6. The method of claim 1, wherein the analyzing step includes comparing the symptoms experienced by the one or more patients before the particular intervention is employed to the symptoms experienced by the one or more patients after the particular intervention is employed.

* * * * *